(12) United States Patent
Petrucci et al.

(10) Patent No.: US 9,161,534 B2
(45) Date of Patent: Oct. 20, 2015

(54) METHODS FOR CLEANING A SURFACE

(75) Inventors: Michael Anthony Petrucci, Destin, FL (US); Thomas B Kelley, Panama City Beach, FL (US)

(73) Assignees: Michael Anthony Petrucci, Destin, FL (US); Donna Jamie Petrucci, Destin, FL (US)

(*) Notice: Subject to any disclaimer, the term of this patent is extended or adjusted under 35 U.S.C. 154(b) by 305 days.

(21) Appl. No.: 13/039,393

(22) Filed: Mar. 3, 2011

(65) Prior Publication Data
US 2012/0058075 A1 Mar. 8, 2012

Related U.S. Application Data

(60) Provisional application No. 61/310,841, filed on Mar. 5, 2010, provisional application No. 61/440,442, filed on Feb. 8, 2011.

(51) Int. Cl.

| | |
|---|---|
| *A01N 37/36* | (2006.01) |
| *A01N 37/02* | (2006.01) |
| *A01N 59/16* | (2006.01) |
| *A01N 65/42* | (2009.01) |
| *A61K 31/19* | (2006.01) |
| *A61K 33/30* | (2006.01) |
| *A61K 36/886* | (2006.01) |
| *A61L 9/01* | (2006.01) |
| *A61P 17/02* | (2006.01) |
| *A61P 17/00* | (2006.01) |
| *A61K 31/194* | (2006.01) |

(52) U.S. Cl.
CPC .............. *A01N 37/36* (2013.01); *A01N 37/02* (2013.01); *A01N 59/16* (2013.01); *A01N 65/42* (2013.01); *A61K 31/19* (2013.01); *A61K 31/194* (2013.01); *A61K 33/30* (2013.01); *A61K 36/886* (2013.01); *A01N 2300/00* (2013.01); *A61K 2300/00* (2013.01)

(58) Field of Classification Search
CPC ... A01N 59/16; A01N 2300/00; A01N 37/02; A01N 37/36; A01N 65/42; A01N 37/00; A61K 31/19; A61K 31/194; A61K 33/30; A61K 36/886

USPC .............. 424/76.8, 94.1, 642, 744, 618, 76.4; 514/494, 574, 557, 783, 887, 928
See application file for complete search history.

(56) References Cited

U.S. PATENT DOCUMENTS

| | | |
|---|---|---|
| 4,595,517 A | 6/1986 | Abadi |
| 4,647,458 A | 3/1987 | Ueno et al. |
| 5,021,096 A | 6/1991 | Abadi |
| 5,108,514 A | 4/1992 | Kisner |
| 5,169,563 A | 12/1992 | Katayama, deceased, et al. |
| 5,468,303 A | 11/1995 | Thomas, Sr. |
| 5,622,708 A * | 4/1997 | Richter et al. ................ 424/405 |
| 5,709,546 A | 1/1998 | Waggoner |
| 5,772,872 A | 6/1998 | Shelhamer |
| 5,772,986 A | 6/1998 | Kross |
| 5,919,375 A | 7/1999 | Sargent et al. |
| 5,989,440 A | 11/1999 | Shimura et al. |
| 6,019,905 A | 2/2000 | Waggoner |
| 6,534,075 B1 | 3/2003 | Hei et al. |
| 7,261,905 B2 * | 8/2007 | Arata et al. ................... 424/618 |
| 7,510,721 B2 | 3/2009 | Roden et al. |
| 2002/0045600 A1 | 4/2002 | Schwarzman |
| 2008/0274209 A1 * | 11/2008 | Smith .......................... 424/642 |
| 2009/0081806 A1 | 3/2009 | Reeves, III et al. |

FOREIGN PATENT DOCUMENTS

| | | |
|---|---|---|
| CA | 1270429 | 6/1990 |
| GB | 245365 | 1/1926 |
| WO | WO 87/04143 | 7/1987 |
| WO | WO 2007/053518 | 5/2007 |

* cited by examiner

*Primary Examiner* — Anna Pagonakis
*Assistant Examiner* — Miriam A Levin
(74) *Attorney, Agent, or Firm* — Blynn L. Shideler; Krisanne Shideler; BLK Law Group

(57) ABSTRACT

A method of killing and removing bacteria, mold, mildew or fungus from a surface or keratin substrate includes contacting the surface with an aqueous solution containing a multi carboxylic alpha hydroxy acid, a mono carboxylic organic acid and optionally Aloe. The aqueous solution has a pH of less than 2. The method can also be used to deodorize fabrics, surfaces or stagnant water. The method can also be used to treat wounds and skin irritations.

9 Claims, No Drawings

METHODS FOR CLEANING A SURFACE

REFERENCE TO RELATED APPLICATION

This application claims the benefit of priority of U.S. Provisional Application Ser. Nos. 61/440,442, filed Feb. 2, 2011 entitled "Novel Methods for Treating Wounds and Skin Irritations" and 61/310,841, filed Mar. 3, 2010 entitled "Novel Methods For Cleaning a Surface"; which are both herein incorporated by reference in their entirety.

BACKGROUND OF THE INVENTION

1. Field of the Invention

The present invention relates to novel formulations that contain materials generally regarded as safe ("GRAS") useful for treating surfaces and as topical skin treatments. In particular, it relates to solutions that are spread on a surface to disinfect, sanitize and deodorize and on keratin substrates to aid in healing wounds and alleviating the symptoms of skin irritation caused by burns, insect and jelly fish bites, and plant irritants such as poison oak and poison ivy.

2. Brief Description of the Prior Art

Low pH compositions and solutions containing acidic compositions are used for various industrial and general household purposes, such as cleaning and sterilizing surfaces and articles of manufacture. Examples include well-known household cleansers and disinfectants, industrial microchip production and cleaning agents, and anti-microbials. To work both effectively and efficiently, these solutions typically contain strong inorganic acids or organic solvents, which present health concerns to the user, may be corrosive to the substances they are designed to clean (e.g. metals) and pose an ecological hazard with respect to disposal.

U.S. Pat. No. 7,510,721 discloses solutions containing acidic compositions that have a pH of less than 1. The solution contains a first inorganic acid that dissociates nearly to completion in water, a second inorganic acid less strong than the first acid, a hydroxy acid having a chelating capability of at least twice the first and second acids; and a permanganate. The acidic compositions may be used in medical, industrial, military and household applications. Plants are constantly challenged by a wide variety of pathogentic organisms including viruses, bacteria, fungi, and menatodes. Attempts have been made to control plant disease by means of disinfections, replacement of the soil, various cultural practices, and control by chemicals. Some plants suffer from detrimental soil-spread diseases, which have not been possible to control owing to restrictions of use of chemical control agents and hazard periods due to possible residues or lack of sufficiently effective products.

About twenty-five (25) percent of all fungal diseases in agricultural and horticulture are caused by powdery mildew phytopathogens.

This problem is exacerbated once fruits and vegetables are picked, as the presence of fungus or mildew on the surface of the fruit or vegetable greatly shortens its shelf life, the time from when it is picked or harvested until it reaches the ultimate consumer.

Due to the vast economic ramifications of fungal propagation in agricultural and horticultural cultivations, a broad spectrum of fungicidal and fungistatic products have been developed for general and specific applications. Such examples are the use of inorganic bicarbonate, carbonate compounds, lecithin, and lime. However, these fungicidal and fungistatic products may be harmful to the environment and may pollute areas such as ground waters.

Further, growers are increasingly reluctant to use chemicals that may cause health problems if consumed by people and are constantly looking for safe materials to treat fruit and vegetables to extend their shelf life.

Thus, there is a need for a safe anti bacterial, mildew or fungal treatment which provides for an inexpensive way to kill and destroy microorganisms on surfaces without harming the environment.

Various treatments for skin irritation are known. For insect bites, such as mosquito bites, treatments such as Calamine lotion, have been used for many years. Cortisone treatment has also been used to treat numerous skin problems, including insect bites.

In addition to insects, there are numerous other sources of skin irritation. For example, numerous plants produce substances that have a toxic or irritating effect on skin. Poison Ivy, poison oak, poison sumac, etc. are only a few examples of many types of plants which have an injurious effect on human skin.

Insects and plants that attack people on land are only one source of skin irritation. There are also many waterborne hazards faced by humans. For individuals who swim in warmer coastal waters, sea lice represent a particularly disagreeable hazard. Sea lice is a commonly used colloquial expression which describes jelly fish larvae. Sea lice lodge themselves under the skin and result in unsightly welts and extremely irritated and sensitive skin. Treatment for sea lice is typically an agent designed to kill the cause of the irritation. The most common remedy being the use of chemicals such as ammonia to kill the offending organisms. While this will eventually resolve the problem, it does not provide any immediate relief to those being bitten by sea lice. Further, the use of ammonia exacerbates the stinging and burning sensation caused by the sea lice and actually increases user discomfort.

U.S. Patent Application Publication No. 2002/0045600 discloses a topical treatment for skin irritation that uses a spray-on liquid or a rub-on lotion based papain skin treatment for relief of symptoms related to skin irritation. Papain is suspended in a water solution that is spread on the surface of the affected area. The liquid solution ensures that the active ingredient contacts the skin without missing spots as may occur when using dry or powdered skin treatments. The papain is an active ingredient extracted from papaya which relieves the skin irritation caused by sea lice, insect bites, etc.

A disadvantage associated with treatments that do not alleviate pain and discomfort is that they create a situation in which the individual scratches the affected area, which further irritates the skin, and prolongs the healing process.

While addressing the basic desirability of treating sea lice to ensure their elimination, the prior art has failed to provide a method of treating skin irritations caused by sea lice, insect bites, etc. and which results in immediate relief of the symptoms.

It would be desirable to have a way to treat skin irritations caused by a variety of environmental conditions, including those conditions caused by waterborne nuisances such as sea lice, and land borne nuisances such as mosquitos, insects, and plants with substances that irritate skin (for example, poison ivy), which would immediately alleviate the pain and discomfort rather than increase it as the prior art treatments such as ammonia have done.

SUMMARY OF THE INVENTION

The present invention is directed to a method of method of killing and removing bacteria, mold, mildew or fungus from a surface. The method includes contacting the surface with an aqueous solution containing a multi carboxylic alpha hydroxy acid and a mono carboxylic organic acid. The aqueous solution often has a pH of less than 2.

The present invention is also directed to a method of deodorizing fabrics, surfaces or stagnant water that includes making an aqueous solution containing a multi carboxylic alpha hydroxy acid and a mono carboxylic organic acid; and applying an effective amount of the aqueous solution to an odorous fabric, surface or stagnant water to minimize an odor. The aqueous solution often has a pH of not more than 2.

The present invention is directed to a treatment composition that contains Aloe, a multi carboxylic alpha hydroxy acid and a mono carboxylic organic acid, often having a pH of less than 2.

The present invention is also directed to a method of treating a wound that includes preparing a treatment composition containing Aloe, a multi carboxylic alpha hydroxy acid and a mono carboxylic organic acid that often has a pH of less than 2; and applying the treatment composition to the wound area.

The present invention is also directed to a method of treating a skin irritation that includes preparing a treatment composition containing Aloe, a multi carboxylic alpha hydroxy acid and a mono carboxylic organic acid that often has a pH of less than 2; and applying the treatment composition to the irritated area of the skin.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the term "active basis" refers to a concentration of additive based on the active solids in the solution.

As used herein, the term "Aloe" refers to, but is not limited to, concentrated Aloe Vera gel that is prepared by extracting biologically active compounds from Aloe vera leaves, including, but not limited to acetylated mannans, polymannans, anthraquinone C-glycosides, anthrones, anthraquinones, lectins, proteins, vitamins and enzymes. Suitable Aloe for use in the invention typically contains water, ployhexanoses; hexans; xylose; arabinose; galactose; glucose; amino acids, including without limitation lysine, histadine, arginine, aspartic acid, threonine, serine, glutamic acid, proline, glycine, analine, valine, methionine, isoleucine, leucine, tyrosine and pheylalanine; and vitamins B-1, B-2, C, niacinamide, B-6 and choline; and enzymes such as amylase and lipase. In embodiments of the invention, the Aloe can have from 5% to 60% solids based on the weight of Aloe, each amino acid, when present, can be present at from 0.5 to 20 ppm based on the Aloe, the vitamins, when present can be present at from 0.5 to 80 ppm based on the Aloe, and the enzymes can be present at from 500 to 2,000 units per 100 ml of Aloe.

As used herein, the term "effective amount" refers to that amount of a composition necessary to bring about a desired result, such as, for example, the amount needed to sanitize a surface, deodorize a substrate, treat a keratin substrate relative to a particular purpose, such as healing a wound or treating an irritation.

As used herein, the term "keratin substrate" refers to skin, nails, horns, and hair containing a structural matrix of fibrous proteins that are capable of forming intra- and intermolecular hydrogen bonds and containing sufficient cysteine or other sulfur-containing amino acids to provide the amount of disulfide bridges for the intended function.

As used herein, the term "skin" unless otherwise indicated, refers to the epidermis of mammals and birds, including, but not limited to humans and domesticated animals.

As used herein, the term "substantially free" is meant to indicate that a material can be present in an incidental amount or that a particular occurrence or reaction only takes place to an insignificant extent, which does not effect desired properties. In other words, the material is not intentionally added to an indicated composition, but may be present at minor or inconsequential levels, for example, because it was carried over as an impurity as part of an intended composition component.

The present invention provides compositions useful in methods of killing and removing bacteria, mold, mildew or fungus from a surface, including keratin substrates. The method includes making an aqueous solution composition containing a multi carboxylic alpha hydroxy acid and a mono carboxylic organic acid. The surface or keratin substrate is then contacted by or with the solution, which kills the bacteria, mold, mildew and/or fungus on the surface. In instances where the solution does not remove the killed bacteria, mold, mildew or fungus, it is removed physically by wiping, scrubbing, high pressure water, and other methods known in the art.

The present invention also provides a method of deodorizing fabrics, surfaces and stagnant water. The method includes making an aqueous solution composition containing a multi carboxylic alpha hydroxy acid and a mono carboxylic organic acid. An effective amount of the aqueous solution is applied to the fabric, surface and stagnant water to eliminate odors caused by bacteria, mold, mildew or fungus.

In various embodiments of the invention, the aqueous solution composition can be used in methods to clean fabrics, clean carpet, disinfect fabrics, surfaces and stagnant water, clean windows, clean circuit boards, and clean wheels.

In other embodiments of the invention, the aqueous solution composition can be used in methods to kill and/or prevent the spread of *e-coli* or *salmonella* bacteria.

In some embodiments of the invention Aloe is added to the aqueous solution composition to provide a treatment composition particularly useful for treating keratin substrates.

In particular embodiments of the invention directed to methods of treating a wound or burn, the aqueous solution composition includes Aloe, a multi carboxylic alpha hydroxy acid and a mono carboxylic organic acid and may have a pH of less than 2. In these embodiments, the aqueous solution is applied to the wound or burn area.

Other particular embodiments of the invention provide a method of treating a skin irritation that includes preparing the aqueous solution composition containing Aloe, a multi carboxylic alpha hydroxy acid and a mono carboxylic organic acid; and applying the aqueous solution composition to the irritated area of the skin.

Generally, the aqueous solution can be sprayed lightly over the area to be treated, in an effective amount to wet or moisten skin or other keratin substrate, a surface or fabric. The aqueous solution is applied to skin or other keratin substrate, a surface or fabric under a predetermined level of pressure.

In embodiments of the invention, the solution typically has a pH of about 2 or lower, and in embodiments of the invention can be less than about 2, in some cases not more than about 1.5 and in other cases not more than about 1.

Suitable multi carboxylic alpha hydroxy acids that can be used in the invention contain from 3 to 12 carbon atoms, two or more carboxylic acid functional groups and at least one hydroxyl group. In embodiments of the invention, the multi carboxylic alpha hydroxy acid used in the aqueous solution of the present method can be one or more selected from citric acid, malic acid, tartaric acid, and combinations thereof.

The multi carboxylic alpha hydroxy acid can be present in the aqueous solution at a level of at least 2, in some cases at least 3, in other cases at least 4, in some instances at least 5, and in other instances at least 6 weight percent. Also, the multi carboxylic alpha hydroxy acid can be present in the aqueous solution at a level of up to 15, in some cases up to 14, in other cases up to 13, in some instances up to 12, in other instances up to 11 and in some situations up to 10 weight percent based on the weight of the aqueous solution. The amount of multi carboxylic alpha hydroxy acid present in the aqueous solution can be any value or range between any of the values recited above.

Suitable mono carboxylic acids that can be used in the invention contain from 1 to 12 carbon atoms and one carboxylic acid functional group. In embodiments of the invention, the mono carboxylic acid used in the aqueous solution of the present method can be one or more selected from fromic acid, acetic acid, propionic acid, butyric acid, valeric acid, caproic acid, enanthic acid, caprylic acid, pelargonic acid, capric acid, and combinations thereof.

The mono carboxylic acid can be present in the aqueous solution at a level of at least 0.5, in some cases at least 1, and in other cases at least 1.5 weight percent. Also, the mono carboxylic acid can be present in the aqueous solution at a level of up to 5, in some cases up to 4.5, and in other cases up to 4, weight percent based on the weight of the aqueous solution. The amount of mono carboxylic acid present in the aqueous solution can be any value or range between any of the values recited above.

In various embodiments of the invention, the aqueous solution can optionally include nonionic surfactants. Suitable nonionic surfactants include, but are not limited to polyethers such as, for example, polyethylene oxide; polypropylene oxide; ethylene oxide-propylene oxide AB block copolymers, ethylene oxide-propylene oxide-ethylene oxide ABA block copolymers, propylene oxide-ethylene oxide-propylene oxide BAB block copolymers and combinations thereof. In aspects of this embodiment, the AB, ABA and ABA block copolymers can include from 20-80% ethylene oxide and 20-80% propylene oxide units by weight. The molecular weight of the polyethers can have a molecular weight in the range from 2,000-20,000. In aspects of this embodiment, the nonionic surfactant can have a hydrophilic-lipophilic balance be in the range of 7-24.

When included, the nonionic surfactants can be present in the aqueous solution at a level of at least 0.001, in some cases at least 0.01, and in other cases at least 0.1 percent by weight and can be present at up to 10, in some cases up to 8, in other cases up to 6, in some instances up to 5 and in other instances up to 4 percent by weight of the aqueous solution. When nonionic surfactants are included in the aqueous solution, they can be present at any value or range between any of the values recited above.

In various embodiments of the invention, the aqueous solution can optionally include a tertiary amine. Suitable tertiary amines include, but are not limited to those having a structure according to $R^1{}_2NR^2$, where each $R^1$ can independently be a $C_1$-$C_3$ alkyl group and $R^2$ can independently be a $C_8$-$C_{30}$ linear or branched alkyl group and combinations thereof.

When included, the tertiary amines can be present in the aqueous solution at a level of at least 0.001, in some cases at least 0.01, and in other cases at least 0.1 percent by weight and can be present at up to 10, in some cases up to 8, in other cases up to 6, in some instances up to 5 and in other instances up to 4 percent by weight of the aqueous solution. When tertiary amines are included in the aqueous solution, they can be present at any value or range between any of the values recited above.

In embodiments of the invention, the aqueous solution can optionally include anionic detersive surfactants. Non-limiting examples of suitable anionic detersive surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine 1 lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium xylene sulfonate and combinations thereof. When included, the anionic detersive surfactants can be present in the aqueous solution at a level of at least 0.001, in some cases at least 0.01, and in other cases at least 0.1 percent by weight and can be present at up to 10, in some cases up to 8, in other cases up to 6, in some instances up to 5 and in other instances up to 4 percent by weight of the aqueous solution. When anionic detersive surfactants are included in the aqueous solution, they can be present at any value or range between any of the values recited above.

In some embodiments, the aqueous solution can include a fragrance and/or odor reducing agent in an amount sufficient to provide its function.

In many embodiments of the invention, the aqueous solution is substantially free of inorganic acids. As used herein, "inorganic acid" refers to compounds that contain at least one hydrogen atom that is capable of dissociating from the compound to form a hydrogen ion in solution and that does not contain a carbon atom. In other embodiments of the invention, inorganic acids are present at less than 2, in some cases less than 1, in other cases less than 0.5, and in some instances less than 0.1 weight percent based on the weight of the aqueous solution.

In some embodiments of the invention where the aqueous solution is used to disinfect and deodorize surfaces and fabrics, the aqueous solution may be substantially free of inorganic salts. As used herein, "inorganic salts" refers to compounds that contain at least one inorganic cation and at least one inorganic anion derived from an inorganic acid. Non-limiting examples of inorganic acids include sodium chloride, calcium chloride, calcium carbonate, and the like. In other embodiments of the invention, inorganic salts are present at less than 2, in some cases less than 1, in other cases less than 0.5, and in some instances less than 0.1 weight percent based on the weight of the aqueous solution.

In various embodiments of the invention, one or more metals or their corresponding salts, in a solution or colloidal states, can be included in the aqueous solution. In many instances the corresponding salts can include, halides, acetates, gluconates, sulfates, phosphates, phosphonates, nitrates, carbonates and combinations thereof. In particular embodiments of the invention, the metals are selected from zinc, magnesium, manganese, silver, gold, and combinations thereof. When includes, the metals or metal salts are present at greater than 0.00001 weight percent and typically constitute less than 1, in some cases less than 0.5, in other cases less than 0.5, and in some instances less than 0.1 weight percent based on the weight of the aqueous solution.

In many embodiments of the invention, the aqueous solution is used to disinfect, deodorize or sanitize surfaces in hospitals, veterinarian clinics, farms, pet stores, horse training facilities, organic food and animal processing plants, farms, and related machinery. Typically, in these embodiments, the aqueous solution includes a multi carboxylic alpha hydroxy acid and a mono carboxylic organic acid, and has a pH of 2 or less.

When used to treat carpet, like ordinary dry cleaning, the carpet can be "spotted" before the general cleaning process, and the aqueous solution can be readily modified, as will be obvious to solve specific problems, such as pet or urine odors and stains, rust, blood, coffee stains, and the like.

In embodiments of the invention, a surface or fabric is contacted by the aqueous solution by applying it as a spray.

In one embodiment of the invention, the aqueous solution is bottled in a spray bottle and sprayed onto a surface or fabric. The aqueous solution can be provided in a spray bottle dispenser as a preventive maintenance type cleaner applied onto surfaces and fabrics. By applying the aqueous solution to the area immediately after soiling, build up of wash area related dirt, such as soap scum, is minimized.

The spray bottle dispenser can include a bottle portion and a spray head portion. The bottle portion has an externally threaded neck portion to which the spray head portion connects by an internally threaded collar. The spray head portion further includes a nozzle portion as well as a housing portion out of which extends a trigger portion for operating a piston to pump fluid inside the housing portion. A dip tube connected to an inlet of the pump extends from the housing portion through the collar portion and into the bottle portion. When the spray head portion is connected to the bottle portion, at least a portion of the dip tube is immersed in the aqueous solution contained in the bottle portion.

In one embodiment of the invention, the surface is contacted by the aqueous solution applied as an aerosol. In aspects of this embodiment, the aerosol is applied from a cylindrical canister that is filled with the aqueous solution and pressurized by air or another propellant.

Suitable canisters are known in the art and typically include a tap valve assembly which includes a collar portion adapted to sealingly fit about a lip.

In embodiments that utilize convention aerosols, a variety of propellants can be used including hydrocarbons such as propane, normal butane, isobutane, mixtures of them, and similar materials. Nitrogen and carbon dioxide can also been used.

Aerosol containers depend upon gas dissolved in the liquid contents of the system to be released from solution to the extent required to occupy the additional space thus created. Consequently, the suitability of a particular gas as a propellant depends upon the degree to which it is soluble in the aqueous solution In some embodiments of the invention, the surface to be treated is contacted by the aqueous solution as a liquid stream. The liquid stream can be applied via a hose, nozzle or spray heads as is readily recognized in the art.

The methods according to the invention can be used to kill bacteria on surfaces and/or deodorize surfaces and fabrics. Non-limiting examples of surfaces that can be treated according to the present methods include the surface of a vegetable, the surface of a fruit, surface of a nut, the exterior surface of a building, a wall, the surface of a water craft, barns, stables, countertops, and shelves.

Thus the present invention provides a method and composition that is organic in nature and is able to control or kill bacteria, fungus, mold and mildew on surfaces.

In embodiments of the invention, the aqueous solution acts as a fungicide and/or bactericide. As a non-limiting example, the aqueous solution can be used to keep pools free of algae. In this embodiment, the acids in the aqueous solution do not evaporate and the test pools are able to be kept free of chlorine or hypochlorite.

In embodiments of the invention, the aqueous solution can be sprayed over the surface of athletic equipment in an effective amount to eliminate the smell of body odor on the equipment.

In embodiments of the invention, the aqueous solution can be sprayed over the surface of green vegetables, such as spinach and beans or nuts in an effective amount to prevent the spread of *e-coli* or *salmonella* bacteria.

In embodiments of the invention, the aqueous solution can be sprayed over the surface of eggs, coating them at the processing plant to inhibit the growth of pathogens and kill *e-coli* and *salmonella*.

In embodiments of the invention, the aqueous solution can be sprayed over surfaces for treating homes with black mold and to inhibit future mold growth.

In embodiments of the invention, the aqueous solution can be sprayed over surfaces for treating showers, wood, windows, vinyl siding, restaurant equipment and coolers to inhibit the growth of pathogens, sanitize, deodorize and generally disinfect the surfaces.

In embodiments of the invention, the aqueous solution can be sprayed over the surface of floors and walls in a locker room in an effective amount to deodorize and prevent the spread of bacteria, mildew and mold.

In embodiments of the invention, the aqueous solution can be sprayed over the surface of marine surfaces, such as boats, bumpers, docks and fabrics in an effective amount to prevent the spread of mold, mildew and other microbes.

In embodiments of the invention, the aqueous solution can be applied by dipping an article, eggs, fruit or vegetable in the aqueous solution in an effective amount for an effective amount of time to deodorize and prevent the spread of bacteria, mildew and mold.

In other embodiments of the invention, the aqueous solution and present methods can be used in kennels and stables to keep them free of bacteria, mildew and mold which cause colic with horses. The methods according to this embodiment can be used any where animals are kept, including, but not limited to pigs, cows, horses, and on milk farms.

The aqueous solution is effective at inhibiting the growth indoors and outside for about 60 to about 90 days.

In embodiments of the invention, the aqueous solution includes Aloe and optionally metals or metal salts and is used to promote faster wound healing, including burns, cuts, bruises, scrapes and topical infections of the skin. Also, the aqueous solution is effective at killing *e-coli, salmonella, listeria, pseudomonas, staph* and methicillin-resistant *staphylococcus aureus* (MRSA), and *aspergillus niger* (black mold).

In particular aspects of the invention, the aqueous solution is effective at treating infections and healing wounds in diabetic patients.

Additionally, the aqueous solution is effective at treating skin irritations, dermatitis, eczema, seborria and psoriasis. It also relieves the itching of poison oak, sumac and ivy, and reduces the itching from insect bites and jelly fish stings, swelling and itching from fire ant bites.

Embodiments of the invention provide a method of treating insect bites, for example mosquito bites and bee stings; skin irritations caused by skin contact with plants that produce substances that have a toxic or irritating effect on skin for example poison Ivy, poison oak, and poison sumac; fire ant bites; and jelly fish stings.

The method includes preparing an aqueous solution containing one or more multi carboxylic alpha hydroxy acids, one or more mono carboxylic organic acids, Aloe and optionally a metal or metal salt as described above and applying the aqueous solution to the irritated area.

The aqueous solution may have a pH of 2 or less.

In many aspects of this embodiment, the metal includes zinc or silver. In many instances, the metal is added as an aqueous solution or colloidal dispersion of a metal salt. As non-limiting examples, the metal salt can be zinc gluconate, silver nitrate or a combination thereof.

The aqueous solution can be sprayed lightly over the area to be treated, or applied to a bandage or wrap, which is then placed over the irritated skin. The amount of aqueous solution used is an effective amount to relieve the skin irritation symptoms.

The aqueous solution is effective at relieving skin irritation symptoms, for example itching and burning sensations and promotes faster healing.

Other embodiments of the invention provide a method of treating fungal infections of the skin, hair and nails, non-limiting examples of which include superficial mycoses and cutaneous mycoses such as athlete's foot fungus.

The method includes preparing an aqueous solution containing one or more multi carboxylic alpha hydroxy acids, one or more mono carboxylic organic acids, Aloe and optionally a metal or metal salt as described above and applying the aqueous solution to the infected area.

The aqueous solution may have a pH of 2 or less.

In many aspects of this embodiment, the metal includes zinc or silver. In many instances, the metal is added as an aqueous solution or colloidal dispersion of a metal salt. As non-limiting examples, the metal salt can be zinc gluconate, silver nitrate or a combination thereof.

The aqueous solution can be sprayed or brushed lightly over the area to be treated. The amount of aqueous solution used is an effective amount to relieve the skin irritation symptoms.

The aqueous solution is effective at relieving fungal infection symptoms, for example itching and burning sensations and promotes faster healing.

Further embodiments of the invention provide a method of treating skin burns. The method includes preparing an aqueous solution containing one or more multi carboxylic alpha hydroxy acids, one or more mono carboxylic organic acids, Aloe and optionally a metal or metal salt as described above and applying the aqueous solution to the damaged area of the skin.

The aqueous solution may have a pH of 2 or less.

In many aspects of this embodiment, the metal includes zinc or silver. In many instances, the metal is added as an aqueous solution or colloidal dispersion of a metal salt. As non-limiting examples, the metal salt can be zinc gluconate, silver nitrate or a combination thereof.

The aqueous solution can be sprayed lightly over the area to be treated, or applied to a bandage or wrap, which is then placed over the irritated skin. The amount of aqueous solution used is an effective amount to relieve the skin irritation symptoms.

The amount of aqueous solution used is an effective amount to relieve pain and promote healing.

The aqueous solution is effective at relieving symptoms, for example pain, itching and burning sensations, preventing infection and promoting faster healing.

Additional embodiments of the invention provide a method of treating wounds, for example, where the skin is torn, cut or punctured; where blunt force trauma causes a contusion; or other instances where a sharp injury damages the skin.

The method includes preparing an aqueous solution containing one or more multi carboxylic alpha hydroxy acids, one or more mono carboxylic organic acids, Aloe and optionally a metal or metal salt as described above and applying the aqueous solution to the damaged area of the skin.

The aqueous solution may have a pH of 2 or less.

In many aspects of this embodiment, the metal includes zinc or silver. In many instances, the metal is added as an aqueous solution or colloidal dispersion of a metal salt. As non-limiting examples, the metal salt can be zinc gluconate, silver nitrate or a combination thereof.

The aqueous solution can be sprayed lightly over the area to be treated, or applied to a bandage or wrap, which is then placed over the wound area. The amount of aqueous solution used is an effective amount to relieve the skin irritation symptoms.

The amount of aqueous solution used is an effective amount to relieve skin discomfort and promote healing.

The aqueous solution is effective at relieving pain and other symptoms, for example itching and burning sensations and promotes faster healing.

The present invention will further be described by reference to the following examples. The following examples are merely illustrative of the invention and are not intended to be limiting. Unless otherwise indicated, all percentages are by weight.

EXAMPLE 1

An aqueous solution was prepared by mixing 8% citric acid and 1% acetic acid with 91% by weight water. The pH of the solution was 1.6.

The aqueous solution was sprayed onto the surface of strawberries that had visible mold on its outer surface. The mold was killed on contact. After rinsing with clean water, the strawberries were suitable for human consumption.

EXAMPLE 2

An aqueous solution was prepared by mixing 8% citric acid and 1% acetic acid with 91% by weight water. The pH of the solution was 1.6.

The aqueous solution was sprayed onto the surface of a boat with visible mold and mildew on its outer surface. The mold and mildew was killed on contact. After rinsing with clean water, the mold and mildew was easily removed from the surface.

EXAMPLE 3

An aqueous solution was prepared by mixing 8% citric acid and 1% acetic acid with 91% by weight water. The pH of the solution was 1.6.

The aqueous solution was sprayed onto the surface of soffit and fascia boards on a house with visible mold and mildew on its surface. The mold and mildew was killed on contact. After rinsing with clean water, the mold and mildew was easily removed from the surface.

EXAMPLE 4

An aqueous solution was prepared by mixing 8% citric acid and 1% acetic acid with 91% by weight water. The pH of the solution was 1.6.

The aqueous solution was sprayed onto the surface of a window with visible mold and mildew on its surface. The mold and mildew was killed on contact. After rinsing with clean water, the mold and mildew was easily removed from the surface.

EXAMPLE 5

An aqueous solution was prepared by mixing 8% citric acid and 1% acetic acid with 91% by weight water. The pH of the solution was 1.6.

The aqueous solution was sprayed onto a cushion with a distinctly musty odor. The musty odor was eliminated after contact with the aqueous solution.

EXAMPLE 6

An aqueous solution was prepared by mixing 8% citric acid and 1% acetic acid with 91% by weight water. The pH of the solution was 1.6.

The aqueous solution was sprayed onto a carpet with a distinctly musty odor. The musty odor was eliminated after contact with the aqueous solution.

EXAMPLE 7

An aqueous solution was prepared by mixing 8% citric acid and 1% acetic acid with 91% by weight water. The pH of the solution was 1.6.

The aqueous solution was sprayed onto a carpet contaminated with cat urine. The urine odor was eliminated after contact with the aqueous solution.

EXAMPLE 8

An aqueous solution was prepared by mixing 8% citric acid and 1% acetic acid acid with 91% by weight water. The pH of the solution was 1.6.

The aqueous solution was sprayed onto football pads that had a distinct body odor smell. The body odor smell was eliminated after contact with the aqueous solution.

EXAMPLE 9

A first aqueous solution (A1) was prepared by mixing 8% citric and 1% acetic with 91% by weight water.

A second aqueous solution (A2) was prepared by mixing 1% acetic acid, 7% citric acid, 1% liquid vitamin zinc (a solution containing 3.75 g/l zinc gluconate), 46% deionized water, and 46% Aloe 2:1 concentrate (Temsha Corp., Vista Calif.) based on the weight of the solution.

The solutions were evaluated for their ability to inhibit and kill pathogens commonly found in the environment. Initially, general aerobic growth media (R2A) was selected for all of the organisms to grow reconstituted control organisms. The organisms were then transferred to an enrichment medium of Laurel Sulfate Broth to maintain the growth of the culture. The final inhibition study was conducted using R2A agar.

Lawn growth (complete plate coverage) was inoculated on two separate plates for each of the nine organisms tested. One plate was not treated in any manner and was used as a control growth plate. The second plate had glass fiber discs impregnated with A1 and A2 solutions applied on top of the lawn growth. Both solutions had a pH of 1.6.

After a period of 2 days at 35° C. for all organisms except *A. niger* and 5 days 20° C. for 5 days for *A. niger*, the plates were examined for evidence of growth inhibition surrounding the impregnated disk.

The following table shows the results for inhibition growth results.

|   | Pathogen | Growth Control | A1 | A2 |
|---|---|---|---|---|
| 1 | *Aspergillus niger* | Positive | Positive | Negative |
| 2 | *Enterobacter aerogenes* | Positive | Negative | Negative |
| 3 | *Enterococcus faecalis* | Positive | Negative | Negative |
| 4 | *Escherichia coli* | Positive | Negative | Negative |
| 5 | *Klebsiella pnuemoniae* | Positive | Negative | Negative |
| 6 | *Listeria monocytogenes* | Positive | Negative | Negative |
| 7 | *Pseudomonas aeruginosa* | Positive | Negative | Negative |
| 8 | *Salmonella enterica* | Positive | Negative | Negative |
| 9 | *Staphlyococcus epidermidis* | Positive | Negative | Negative |

The data demonstrate that the application of A2 was satisfactory in the inhibition of growth of all the tested pathogens as evident with a large halo surrounding the impregnated disk where there is no evidence organism growth. A1 was satisfactory in the inhibition of growth of all the tested pathogens with exception of *A. niger*.

EXAMPLE 10

An aqueous solution was prepared by mixing 1% acetic acid, 7% citric acid, 1% liquid vitamin zinc (a solution containing 3.75 g/l zinc gluconate), 46% deionized water, and 46% Aloe 2:1 concentrate (Temsha Corp., Vista Calif.) based on the weight of the solution. The pH of the solution was 1.6.

A diabetic patient had an open wound on his leg that was not healing in response to conventional treatment. The progress of the infection indicated that it was near the point that the leg would have to be amputated. After showering and drying, the aqueous solution was wiped over the wound. This procedure was repeated 2-3 times a day. After 7 days of treatment, the size of the wound had decreased 50% from its original size. After 14 days of treatment, the size of the wound was 25% of its original size. After 45 days, the wound was healed.

EXAMPLE 11

An aqueous solution was prepared by mixing 1% acetic acid, 7% citric acid, 1% liquid vitamin zinc (a solution containing 3.75 g/l zinc gluconate), 46% deionized water, and 46% Aloe 2:1 concentrate (Temsha Corp., Vista Calif.) based on the weight of the solution. The pH of the solution was 1.6.

A patient had an itchy rash from poison ivy on his arm. After showering and drying, the aqueous solution was wiped over the rash. The itch sensation immediately went away. This procedure was repeated for three days after which time the rash was completely gone.

EXAMPLE 12

An aqueous solution was prepared by mixing 1% acetic acid, 7% citric acid, 1% liquid vitamin zinc (a solution containing 3.75 g/l zinc gluconate), 46% deionized water, and 46% Aloe 2:1 concentrate (Temsha Corp., Vista Calif.) based on the weight of the solution. The pH of the solution was 1.6.

A patient had an itchy athlete's foot fungus on his toes. After showering and drying, the aqueous solution was wiped over the irritated area. The itch sensation immediately went away. This procedure was repeated for three days after which time the condition was completely removed.

EXAMPLE 13

An aqueous solution was prepared by mixing 1% acetic acid, 7% citric acid, 1% liquid vitamin zinc (a solution containing 3.75 g/l zinc gluconate), 46% deionized water, and 46% Aloe 2:1 concentrate (Temsha Corp., Vista Calif.) based on the weight of the solution. The pH of the solution was 1.6.

A patient had a jelly fish sting on his arm. After showering and drying, the aqueous solution was wiped over the irritated area. The pain sensation immediately went away. This procedure was repeated for three days after which time all indications of the sting were gone.

The present invention has been described with reference to specific details of particular embodiments thereof. It is not intended that such details be regarded as limitations upon the scope of the invention except insofar as and to the extent that they are included in the accompanying claims and equivalents thereof.

We claim:

1. A method of treating a keratin substrate comprising:
   preparing an aqueous solution consisting of:
   water,
   a multi carboxylic alpha hydroxy acid, wherein the multi carboxylic alpha hydroxy acid is one or more selected from the group consisting of citric acid, malic acid, tartaric acid, and combinations thereof and is present in the aqueous solution at from 2 to 15 weight percent,
   a mono carboxylic organic acid, wherein the mono carboxylic organic acid is one or more selected from the group consisting of acetic acid, propionic acid, butyric acid, valeric acid, caproic acid, enanthic acid, caprylic acid, pelargonic acid, capric acid, and combinations thereof and is present in the aqueous solution at from 0.5 to 5 weight percent,
   Aloe, wherein the Aloe comprises water, one or more sugars, one or more proteins, one or more amino acids, one or more vitamins and one or more enzymes, and wherein the Aloe is present in the aqueous solution at from 5 to 70 weight percent, and
   a metal or metal salt, wherein the metal is selected from the group consisting of zinc, magnesium, manganese, gold, and combinations thereof and the metal salt is selected from the group consisting of halides, acetates, gluconates, sulfates, phosphates, phosphonates, nitrates, carbonates and combinations thereof;
   wherein the aqueous solution has a pH of 2 or less;
   wherein the aqueous solution is substantially free of inorganic acids; and
   applying the aqueous solution to the keratin substrate.

2. The method according to claim 1, wherein the metal is zinc and the metal salt is zinc gluconate.

3. The method according to claim 1, wherein the multi carboxylic alpha hydroxy acid is citric acid.

4. The method according to claim 1, wherein the mono carboxylic acid is acetic acid.

5. The method according to claim 1, wherein the aqueous solution is applied to a keratin substrate selected from the group consisting of a burn, a wound area or a skin irritation.

6. The method according to claim 5, wherein the wound area is from a wound of a diabetic patient.

7. The method according to claim 5, wherein the skin irritation is caused by one or more selected from the group consisting of burns, dermatitis, eczema, seborria, psoriasis, poison oak, poison sumac, poison ivy, jelly fish stings, and fire ant bites.

8. The method according to claim 1, wherein the aqueous solution is applied by being sprayed over the keratin substrate.

9. The method according to claim 1, wherein the aqueous solution is applied by being applied to a bandage or wrap, which is then placed over the keratin substrate.

* * * * *